(12) United States Patent
van der Welde

(10) Patent No.: US 7,101,369 B2
(45) Date of Patent: Sep. 5, 2006

(54) TRIAXIAL ANTENNA FOR MICROWAVE TISSUE ABLATION

(75) Inventor: Daniel W. van der Welde, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 84 days.

(21) Appl. No.: 10/834,802

(22) Filed: Apr. 29, 2004

(65) Prior Publication Data

US 2005/0245919 A1 Nov. 3, 2005

(51) Int. Cl.
 *A61B 18/04* (2006.01)
 *A61B 18/18* (2006.01)
 *A61F 2/00* (2006.01)

(52) U.S. Cl. .................. 606/33; 606/41; 607/101; 607/154; 607/156

(58) Field of Classification Search ............ 606/32–35, 606/40–41, 45–50; 607/101–102, 154, 156
See application file for complete search history.

(56) References Cited

U.S. PATENT DOCUMENTS

| 4,446,874 | A | * | 5/1984 | Vaguine ............... 607/156 |
| 4,534,347 | A | * | 8/1985 | Taylor ................. 606/33 |
| 5,026,959 | A | * | 6/1991 | Ito et al. .............. 219/690 |
| 5,167,619 | A | * | 12/1992 | Wuchinich ............ 604/22 |
| 5,275,597 | A | * | 1/1994 | Higgins et al. ........ 606/33 |
| 5,358,515 | A | | 10/1994 | Hurter et al. |
| 5,369,251 | A | * | 11/1994 | King et al. ........... 219/695 |
| 5,405,346 | A | | 4/1995 | Grundy et al. |
| 5,531,677 | A | * | 7/1996 | Lundquist et al. ..... 604/22 |
| 5,599,295 | A | * | 2/1997 | Rosen et al. .......... 604/22 |
| 5,995,875 | A | * | 11/1999 | Blewett et al. ........ 607/98 |
| 6,106,524 | A | * | 8/2000 | Eggers et al. ......... 606/50 |
| 6,325,796 | B1 | * | 12/2001 | Berube et al. ........ 606/33 |
| 6,355,033 | B1 | * | 3/2002 | Moorman et al. ..... 606/33 |
| 6,427,089 | B1 | * | 7/2002 | Knowlton ............ 607/101 |
| 6,652,520 | B1 | | 11/2003 | Moorman et al. |
| 6,770,070 | B1 | * | 8/2004 | Balbierz .............. 606/41 |
| 6,878,147 | B1 | | 4/2005 | Prakash et al. |
| 2003/0065319 | A1 | | 4/2003 | Wellman |

FOREIGN PATENT DOCUMENTS

| EP | 1 186 274 A2 | 3/2002 |
| WO | WO 03/039385 | 5/2003 |
| WO | WO 03/088806 | 10/2003 |
| WO | WO 03/088858 | 10/2003 |

* cited by examiner

*Primary Examiner*—Linda C. M. Dvorak
*Assistant Examiner*—Alex Toy
(74) *Attorney, Agent, or Firm*—Boyle Fredrickson Newholm Stein & Gratz S.C.

(57) ABSTRACT

An improved antenna for microwave ablation uses a triaxial design which reduces reflected energy allowing higher power ablation and/or a smaller diameter feeder line to the antenna.

21 Claims, 1 Drawing Sheet

TRIAXIAL ANTENNA FOR MICROWAVE TISSUE ABLATION

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates to medical instruments for ablating tissue, and in particular to a microwave probe for ablation of tumors and the like.

Microwave ablation (MWA), like radio frequency ablation (RFA), uses localized heating to cause tissue necrosis. However, MWA can produce greater and more rapid heating and can easily support the use of multiple probes because current flow between the probes can be limited. The mode of heating in MWA also eliminates ground pads and charring concerns.

Unfortunately, current MFA equipment produces relatively small lesions because of practical limits in power and treatment time. Power is limited by the current carrying capacity of the small gauge feeder line as it passes through the patient to the site of the necrosis. Larger feeder lines are undesirable because they are not easily inserted percutaneously. Heating of the feeder line at high powers can also lead to burns around the insertion point of the MWA probe.

BRIEF SUMMARY OF THE INVENTION

The present invention provides a triaxial microwave probe design for MWA where the outer conductor allows improved tuning of the antenna to reduce reflected energy through the feeder line. This improved tuning reduces heating of the feeder line allowing more power to be applied to the tissue and/or a smaller feed line to be used. Further, the outer conductor may slide with respect to the inner conductors to permit adjustment of the tuning in vivo to correct for effects of the tissue on the tuning.

Specifically, the present invention provides a probe for microwave ablation having a first conductor and a tubular second conductor coaxially around the first conductor but insulated therefrom. A tubular third conductor is fit coaxially around the first and second conductors. The first conductor may extend beyond the second conductor into tissue when a proximal end of the probe is inserted into a body for microwave ablation. The second conductor may extend beyond the third conductor into the tissue to provide improved tuning of the probe limiting power dissipated in the probe outside of the exposed portions of the first and second conductors.

Thus, it is one object of at least one embodiment of the invention to provide improved tuning of an MWA device to provide greater power to a lesion without risking damage to the feed line or burning of tissue about the feed line and/or to allow smaller feed lines in microwave ablation.

The third tubular conductor may be a needle for insertion into the body. The needle may have a sharpened tip and may use an introducer to help insert it.

Thus, it is another object of at least one embodiment of the invention to provide a MWA probe that may make use of normal needle insertion techniques for placement of the probe.

It is another object of at least one embodiment of the invention to provide a rigid outer conductor that may support a standard coaxial for direct insertion into the body.

The first and second conductors may fit slidably within the third conductor.

It is another object of at least one embodiment of the invention to provide a probe that facilitates tuning of the probe in tissue by sliding the first and second conductors inside of a separate introducer needle.

The probe may include a lock attached to the third conductor to adjustably lock a sliding location of the first and second conductors with respect to the third conductor.

It is thus another object of at least one embodiment of the invention to allow locking of the probe once tuning is complete.

The probe may include a stop attached to the first and second conductors to abut a second stop attached to the third conductor to set an amount the second conductor extends beyond the tubular third conductor into tissue. The stop may be adjustable.

Thus, it is another object of at least one embodiment of the invention to provide a method of rapidly setting the probe that allows for tuning after a coarse setting is obtained.

The second conductor may extend beyond the third conductor by an amount L1 and the first conductor may extend beyond the second conductor by an amount L2 and L1 and L2 may be multiples of a quarter wavelength of a microwave frequency received by the probe.

It is thus another object of at least one embodiment to promote a standing wave at an antenna portion of the probe.

These particular objects and advantages may apply to only some embodiments falling within the claims and thus do not define the scope of the invention.

DETAILED DESCRIPTION OF THE PREFERRED EMBODIMENT

Figure 1:
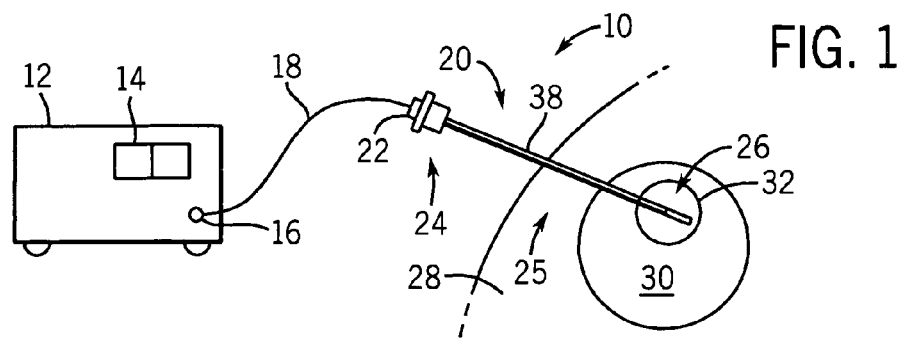
FIG. 1 is a schematic representation of a microwave power supply attached to a probe of the present invention for percutaneous delivery of microwave energy to a necrosis zone within an organ.

Referring now to FIG. 1, a microwave ablation device 10 per the present invention includes a microwave power supply 12 having an output jack 16 connected to a flexible coaxial cable 18 of a type well known in the art. The cable 18 may in turn connect to a probe 20 via a connector 22 at a distal end 24 of the probe 20.

The probe 20 provides a shaft 38 supporting at a proximal end 25 an antenna portion 26 which may be inserted percutaneously into a patient 28 to an ablation site 32 in an organ 30 such as the liver or the like.

The microwave power supply 12 may provide a standing wave or reflected power meter 14 or the like and in the preferred embodiment may provide as much as 100 watts of microwave power of a frequency of 2.45 GHz. Such microwave power supplies are available from a wide variety of commercial sources including as Cober-Muegge, LLC of Norwalk, Conn., USA.

Figure 2:
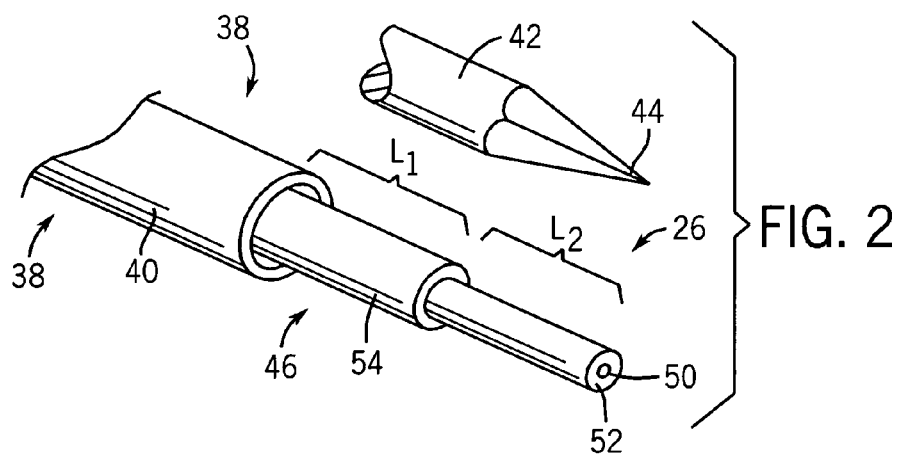
FIG. 2 is a perspective fragmentary view of the proximal end of the probe of FIG. 1 showing exposed portions of a first and second conductor slideably received by a third conductor and showing a sharpened introducer used for placement of the third conductor.

Referring now to FIGS. 1 and 2, generally a shaft 38 of the probe 20 includes an electrically conductive tubular needle 40 being, for example, an 18-gauge needle of suitable length to penetrate the patient 28 to the ablation site 32 maintaining a distal end 24 outside of the patient 28 for manipulation.

Either an introducer 42 or a coaxial conductor 46 may fit within the needle 40. The introducer 42 may be a sharpened rod of a type well known in the art that plugs the opening of the needle 40 and provides a point 44 facilitating the insertion of the probe 20 through tissue to the ablation site 32. The needle 40 and introducer 42 are of rigid material, for example, stainless steel, providing strength and allowing easy imaging using ultrasound or the like.

The coaxial conductor 46 providing a central first conductor 50 surrounded by an insulating dielectric layer 52 in turn surrounded by a second outer coaxial shield 54. This outer shield 54 may be surrounded by an outer insulating dielectric not shown in FIG. 2 or may be received directly into the needle 40 with only an insulating air gap between the two. The coaxial conductor 46 may, for example, be a low loss 0.86-millimeter coaxial cable.

Referring still to FIG. 2, the central conductor 50 with or without the dielectric layer 52, extends a distance L2 out from the conductor of the shield 54 whereas the shield 54 extends a distance L1 out from the conductor of the needle 40. L1 is adjusted to be an odd multiple of one quarter of the wavelength of the frequency of the microwave energy from the power supply 12. Thus the central conductor 50 in the region of L2 provides a resonant monopole antenna having a peak electrical field at its proximal end and a minimal electric field at the end of the shield 54 as indicated by 56.

At 2.45 GHz, the length L2 could be as little as 4.66 millimeters. Preferably, however, a higher multiple is used, for example, three times the quarter wavelength of the microwave power making L2 approximately fourteen millimeters in length. This length may be further increased by multiple half wavelengths, if needed.

Figure 3:
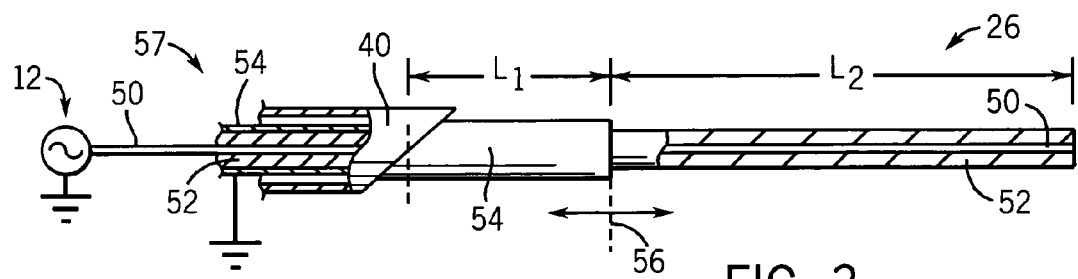
FIG. 3 is a fragmentary cross sectional view of the probe of FIG. 2 showing connection of the microwave power supply to the first and second conductors.

Referring to FIG. 3, the length L1 is also selected to be an odd multiple of one quarter of the wavelength of the frequency of the microwave energy from the power supply 12. When needle 40 has a sharpened or bevel cut tip, distance L1 is the average distance along the axis of the needle 40 of the tip of needle 40.

The purpose of L1 is to enforce a zero electrical field boundary condition at line 56 and to match the feeder line 56 being a continuation of coaxial conductor 46 within the needle 40 to that of the antenna portion 26. This significantly reduces reflected energy from the antenna portion 26 into the feeder line 56 preventing the formation of standing waves which can create hot spots of high current. In the preferred embodiment, L1 equals L2 which is approximately fourteen millimeters.

The inventors have determined that the needle 40 need not be electrically connected to the power supply 12 or to the shield 54 other than by capacitive or inductive coupling. On the other hand, small amounts of ohmic contact between shield 54 and needle 40 may be tolerated.

Figure 4:
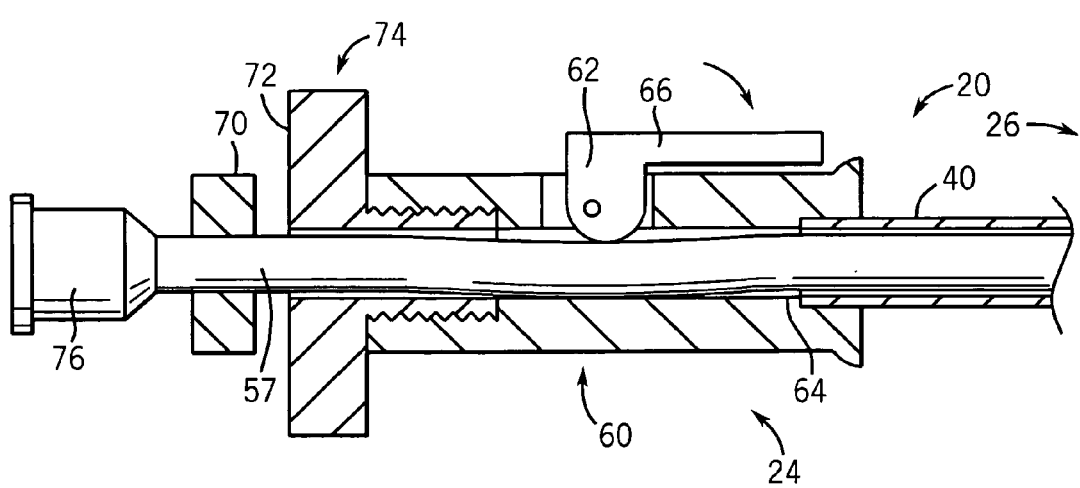
FIG. 4 is a cross sectional view of an alternative embodiment of the probe showing a distal electric connector plus an adjustable stop thumb screw and lock for tuning the probe.

Referring now to FIGS. 1, 2 and 4, during use, the combination of the needle 40 and introducer 42 are inserted into the patient 28, and then the introducer 42 is withdrawn and replaced by a the coaxial conductor 46 so that the distance L2 is roughly established. L2 has been previously empirically for typical tissue by trimming the conductor 50 as necessary.

The distal end 24 of needle 40 may include a tuning mechanism 60 attached to the needle 40 and providing an inner channel 64 aligned with the lumen of the needle 40. The tuning mechanism provides at its distal end, a thumbwheel 72 having a threaded portion received by corresponding threads in a housing of the tuning mechanism and an outer knurled surface 74. A distal face of the thumbwheel provides a stop that may abut a second stop 70 being clamped to the coaxial conductor 46 thread through the tuning mechanism 60 and needle 40. When the stops 70 and on thumbwheel 72 abut each other, the coaxial conductor 46 will be approximately at the right location to provide for extension L1. Rotation of the thumbwheel 72 allows further retraction of the coaxial conductor 46 to bring the probe 20 into tuning by adjusting L1. The tuning may be assessed by observing the reflected power meter 14 of FIG. 1 and tuning for reduced reflected energy.

The tuning mechanism 60 further provides a cam 62 adjacent to the inner channel 64 through which the coaxial conductor 46 may pass so that the cam 62 may press and hold the coaxial conductor 46 against the inner surface of the channel 64 when a cam lever 66 is pressed downwards 68. Thus, once L1 is properly tuned, the coaxial conductor 46 may be locked in position with respect to needle 40.

The distal end of the coaxial conductor 46 may be attached to an electrical connector 76 allowing the cable 18 to be removably attached to disposable probes 20.

The present invention provides as much as a ten-decibel decrease in reflected energy over a simple coaxial monopole in simulation experiments and can create a region of necrosis at the ablation site 32 greater than two centimeters in diameter.

It is specifically intended that the present invention not be limited to the embodiments and illustrations contained herein, but include modified forms of those embodiments including portions of the embodiments and combinations of elements of different embodiments as come within the scope of the following claims.

I claim:

1. A probe for microwave ablation comprising:
   a first conductor;
   a tubular second conductor coaxially around the first conductor but insulated therefrom;
   a tubular third conductor coaxially around the first and second conductors;
   a tuning mechanism having a locked state fixedly holding the third conductor against axial movement with respect to the first and second conductors and having a unlocked state allowing axial movement between the third conductor and the first and second conductors
   wherein the first conductor extends beyond the second conductor into tissue, when a distal end of the probe is inserted into a body for microwave ablation, to promote microwave frequency current flow between the first and second conductors through the tissue; and
   wherein the second conductor may be adjusted by the tuning mechanism to extend beyond the third conductor into tissue when an end of the probe is inserted into the body for microwave ablation to provide improved tuning of the probe limiting power dissipated in the probe outside of exposed portions of the first and second conductors.

2. The probe of claim 1 wherein the tubular third conductor is a needle for insertion into the body.

3. The probe of claim 2 wherein the needle has a sharpened tip.

4. The probe of claim 2 including an introducer removably received by the tubular third conductor to assist in penetration of the body by the needle.

5. The probe of claim 1 wherein the third conductor is stainless steel.

6. The probe of claim 1 wherein the first and second conductors fit slidably within the third conductor.

7. The probe of claim 6 further including a first stop attached to the first and second conductors to abut a first stop attached to the third conductor to set an amount the second conductor extends beyond the tubular third conductor into tissue.

8. The probe of claim 7 wherein the second stop is adjustable.

9. The probe of claim 1 wherein the first conductor extends beyond the second conductor by L2 and the second conductor extends beyond the third conductor by L1 wherein L1 and L2 are odd multiples of a quarter wavelength of a microwave frequency received by the probe.

10. The probe of claim 1 wherein the first conductor extends beyond the second conductor by L2 and the second conductor extends beyond the third conductor by L1 wherein L1 equals L2.

11. The probe of claim 1 wherein a portion of the first conductor extending beyond the second conductor is electrically insulated.

12. The probe of claim 1 wherein the third conductor has an opening smaller than fourteen gauge.

13. The probe of claim 1 including a connector for applying a source of microwave energy to a portion of the probe outside the body.

14. A method of microwave ablation comprising the steps of:
   (a) inserting a probe into a body, the probe having a first conductor; a tubular second conductor coaxially around the first conductor, but insulated therefrom; and a tubular third conductor coaxially around the first and second conductors, wherein the first conductor extends a length L2 from the second conductor and the second conductor extends a length L1 from the third conductor;
   (b) tuning the probe by adjusting L1 with respect to L2 to reduce reflected power;
   (c) applying microwave electrical power across the first and second conductors to induce current flow between exposed portions of the first and second conductors ablating tissue in a region of exposed portions of the first and second conductors.

15. The method of claim 14 wherein the microwave power is in excess of 70 watts.

16. The method of claim 14 wherein step (a) comprises the steps of inserting an introducer into the third conductor and inserting a combination of the third conductor and the introducer percutaneously into the body, withdrawing the introducer and inserting instead the first and second conductors, adjusting the length L2 according to a reflected microwave energy.

17. The method of claim 16 further including the step of locking the first and second conductors in place in the third conductor.

18. The method of claim 14 wherein L1 and L2 are odd multiples of a quarter wavelength of a microwave frequency received by the probe.

19. The method of claim 18 wherein L1 equals L2.

20. The method of claim 14 wherein the third conductor is smaller than 14 gauge.

21. A probe for microwave ablation comprising:
   a first conductor;
   a tubular second conductor coaxially around the first conductor but insulated therefrom;
   a tubular third conductor coaxially around the first and second conductors;
   wherein the first conductor extends beyond the second conductor by a distance L2 and the second conductor extends beyond the third conductor by a distance L1 wherein L1 and L2 are odd multiples of a quarter wavelength of a microwave frequency received by the probe within tissue.

* * * * *

UNITED STATES PATENT AND TRADEMARK OFFICE
CERTIFICATE OF CORRECTION

| | | |
|---|---|---|
| PATENT NO. | : 7,101,369 B2 | Page 1 of 1 |
| APPLICATION NO. | : 10/834802 | |
| DATED | : September 5, 2006 | |
| INVENTOR(S) | : Daniel W. van der Weide | |

It is certified that error appears in the above-identified patent and that said Letters Patent is hereby corrected as shown below:

On the Title Page:

Item (75) Inventor, amend the inventor's name to read -- Daniel W. van der Weide --.

Signed and Sealed this
Twenty-eighth Day of August, 2012

David J. Kappos
*Director of the United States Patent and Trademark Office*